(12) United States Patent
Reynaud et al.

(10) Patent No.: US 10,684,231 B2
(45) Date of Patent: Jun. 16, 2020

(54) PORTABLE SCANNING DEVICE FOR ASCERTAINING ATTRIBUTES OF SAMPLE MATERIALS

(71) Applicant: BRITESCAN, LLC, Petaluma, CA (US)

(72) Inventors: Danica T. H. Reynaud, Cotati, CA (US); Daniel D. Reynaud, Cotati, CA (US)

(73) Assignee: BRITESCAN, LLC, Petaluma, CA (US)

( * ) Notice: Subject to any disclaimer, the term of this patent is extended or adjusted under 35 U.S.C. 154(b) by 0 days.

(21) Appl. No.: 16/534,847

(22) Filed: Aug. 7, 2019

(65) Prior Publication Data

US 2020/0049633 A1   Feb. 13, 2020

Related U.S. Application Data

(60) Provisional application No. 62/715,736, filed on Aug. 7, 2018.

(51) Int. Cl.
G01N 21/88 (2006.01)
G01N 33/00 (2006.01)
(Continued)

(52) U.S. Cl.
CPC ..... *G01N 21/8851* (2013.01); *G01N 33/0098* (2013.01); *G06F 3/0488* (2013.01);
(Continued)

(58) Field of Classification Search
CPC ........... G01N 33/0098; G01N 21/8851; G01N 2021/8887; G06T 7/0002; G06F 3/0488;
(Continued)

(56) References Cited

U.S. PATENT DOCUMENTS 4,236,192 A * 11/1980 Duggan ................ G03B 15/02
362/11
2005/0145048 A1 * 7/2005 Moir .................... B01L 3/50825
73/865.6
(Continued)

FOREIGN PATENT DOCUMENTS

WO    WO-2013192377 A1 * 12/2013

OTHER PUBLICATIONS

Brosnan T. et al. 2017. "Improving quality inspection of food products by computer vision—a review" Agric Rev, 38: 94-102.
(Continued)

*Primary Examiner* — Anner N Holder
(74) *Attorney, Agent, or Firm* — Perkins Coie LLP

(57) ABSTRACT

The disclosed embodiments include at least one system, method, and device for ascertaining attributes of sample material. A method includes enabling a scanning device to capture images of samples placed on an internal surface of the scanning device. The captured images can be communicated over a communications network to a service (e.g., cloud-based service) that can detect features in the captured images in accordance with artificial intelligence techniques to determine attributes of a sample material such as authenticity, purity, or quality. The attributes of the sample material can be certified and communicated for display on a computer, mobile device (e.g., phone, tablet) or scanning device or with interested third-parties.

29 Claims, 12 Drawing Sheets

(51) Int. Cl.
    *G06F 3/0488*     (2013.01)
    *G06K 9/46*     (2006.01)
    *G06K 9/60*     (2006.01)
    *G06T 7/00*     (2017.01)
    *H04N 5/225*     (2006.01)
    *H04N 5/232*     (2006.01)
    *H04N 7/18*     (2006.01)

(52) U.S. Cl.
    CPC ............... *G06K 9/46* (2013.01); *G06K 9/60* (2013.01); *G06T 7/0002* (2013.01); *H04N 5/2253* (2013.01); *H04N 5/23216* (2013.01); *H04N 7/183* (2013.01); *G01N 2021/8887* (2013.01); *H04N 5/23222* (2013.01)

(58) Field of Classification Search
    CPC .. H04N 5/2253; H04N 5/23216; H04N 7/183; H04N 5/23222; G06K 9/60; G06K 9/46
    See application file for complete search history.

(56) References Cited

U.S. PATENT DOCUMENTS

| | | | | |
|---|---|---|---|---|
| 2006/0204121 A1* | 9/2006 | Bryll | ..................... | G06K 9/6288 382/255 |
| 2009/0010804 A1* | 1/2009 | Withrow, III | ........ | A61B 5/0002 422/68.1 |
| 2011/0052019 A1* | 3/2011 | Moshe | ..................... | G06K 9/46 382/128 |
| 2012/0026313 A1* | 2/2012 | Frentz | ..................... | G02B 5/32 348/79 |
| 2013/0322741 A1* | 12/2013 | Lee | ..................... | G06K 9/6256 382/159 |
| 2014/0227774 A1* | 8/2014 | Guthrie | .................. | C12M 41/36 435/288.7 |
| 2014/0350395 A1* | 11/2014 | Shachaf | ................ | G06T 7/0012 600/431 |
| 2015/0072371 A1* | 3/2015 | Marugame | ......... | G01N 33/4833 435/29 |
| 2015/0177147 A1* | 6/2015 | Mangan | ................. | G01N 33/04 250/432 R |
| 2016/0350914 A1* | 12/2016 | Champlin | ............. | G06T 7/0012 |
| 2017/0154218 A1* | 6/2017 | Kisters | ............... | G07C 9/00015 |
| 2017/0205385 A1* | 7/2017 | Prystupa | ................ | G01N 33/12 |
| 2017/0285320 A1* | 10/2017 | Fletcher | ............. | G02B 21/0008 |
| 2018/0003558 A1* | 1/2018 | Goldring | ............... | G01J 3/0291 |
| 2018/0084185 A1* | 3/2018 | Lu | ..................... | H04N 5/23212 |
| 2018/0172510 A1* | 6/2018 | Rosen | ................... | G01J 3/0291 |
| 2018/0240641 A1* | 8/2018 | Mikami | .................. | H01J 37/20 |
| 2018/0322660 A1* | 11/2018 | Smith | .................. | G06K 9/6267 |
| 2019/0096945 A1* | 3/2019 | Lu | ..................... | H01L 27/14627 |

OTHER PUBLICATIONS

Chopde S, et al. 2017. "Developments in computer vision system, focusing on its applications in quality inspection of fruits and vegetables—a review" Agric Rev, 38: 94-102.

Cubero S, et. al. 2011. "Advances in Machine Vision Applications for Automatic Inspection and Quality Evaluation of Fruits and Vegetables" Food Bioprocess Technol 4:487-504.

Krishna KP, et al. 2012. "Machine vision system: a tool for quality inspection of food and agricultural products" J Food Sci Technol 49(2):123-141.

Kumar N, et al. 2012. "Leafsnap: a computer vision system for automatic plant species identification" Computer Vision —ECCV: 502-516.

Rateni G, et al. 2017. Smartphone-based food diagnostic technologies: a review. Sensors, 17: 1453.

Van Horn G, et. al. 2018. "The iNaturalist Species Classification and Detection Dataset" IEEE/CVF Conference on Computer Vision and Pattern Recognition Jun. 18-23, 2018. 10 pages.

Wäldchen J., et al. 2018. "Plant species identification using computer vision techniques: a systematic literature review" Arch Computat Methods Eng, 2025: 507-543.

AgShift, "AgShift—Harness Data. Harvest Profits." Retrieved online at http://www.agshift.com/ Aug. 8, 2019. 1 page.

Bext360, "Best360—Every. Single. Step." Retrieved online at http://www.bext360.com/ Aug. 8, 2019. 2 pages.

Consumer Physics, "SCiO—The World's First Pocket Sized Molecular Sensor" Retrieved online at https://www.consumerphysics.com/ Aug. 8, 2019. 1 page.

Dillenberger, D. "Pairing AI with Optical Scanning for Real-World Product Authentication" May 23, 2018. Retrieved online at https://www.ibm.com/blogs/research/2018/05/ai-authentication-verifier/ Aug. 8, 2019. 5 pages.

IBM, "5 in 5: Crypto anchors and blockchain" Retrieved online at https://www.research.ibm.com/5-in-5/crypto-anchors-and-blockchain/ Aug. 8, 2019. 10 pages.

Nima, "Nima—A Portable Gluten Tester" Retrieved online at https://www.nimasensor.com/ Aug. 8, 2019. 9 pages.

Tellspec, "Food Analysis, Food Safety, Food Database, Food Security" Retrieved online at http://tellspec.com/eng/. 2 pages.

* cited by examiner

PORTABLE SCANNING DEVICE FOR ASCERTAINING ATTRIBUTES OF SAMPLE MATERIALS

CROSS-REFERENCE TO RELATED APPLICATION

This application claims priority to U.S. provisional patent application Ser. No. 62/715,736, filed on Aug. 7, 2018 and titled "TECHNOLOGY FOR ASCERTAINING THE QUALITY AND AUTHENTICITY OF PLANT MATERIALS," which is incorporated herein in its entirety by this reference thereto.

TECHNICAL FIELD

The disclosed teachings relate to a standalone or distributed system including a portable scanning device that can capture images of sample materials and reliably ascertain attributes of the sample materials based on image data.

BACKGROUND

Biological materials are sourced and used throughout developed and developing countries for consumption, as home remedies, and in drug products. Examples include plant materials such as herbs (e.g., parsley) and spices (e.g., cinnamon) and animal materials such as meat and fish. Accordingly, there is a large and distributed global market for certain materials. The materials are typically pre-processed at their sources before distribution to suppliers, manufacturers, retailers, or consumers. For example, plant and animal material may be fresh, dried, cooked, whole, chopped, minced, ground, etc.

Attributes such as the color, size, shape and texture of the material may vary depending upon the genetics of the individual species and the natural conditions when and where the plant material is grown or animal is raised. Examples include the geographic region for cultivation, soil composition, water quality, weather conditions including temperature and humidity, sunshine intensity, and growth period. In another example, material may be contaminated with hazardous impurities such as animal fecal matter, contaminants such as rocks and sticks, or adulterated with fillers such as rice or soy powder.

As a result, intermediaries in a distribution chain of commerce seek to ascertain the attributes (e.g., authenticity, purity, quality) of materials. In conventional techniques, the attributes of materials are subjectively judged based on a skilled person's experience by observing the shape and color of a sample, in smelling flavor and/or via chewing material. As a result, conventional techniques are unreliable and inconsistent because people are not uniformly trained to evaluate diverse materials.

Existing systems that can provide reliable and consistent results involve complex and cost-prohibitive machinery operated by highly-skilled technicians. Those systems that can reliably test quality and authenticity at the chemical or genetic level to determine purity and contaminants are non-portable and are implemented in a few scientific laboratories or at manufacturing facilities. Mobile diagnostic testing systems can rely on expensive optical sensors and equipment (e.g. FTIR and NIR spectrophotometers), require adherence of costly and destructive optical signatures to materials, and require technical experts to develop databases and to operate. As a result, reliable, affordable, and mobile techniques are unavailable to laypeople. Consequently, for example, herbs sourced in developing countries and shipped to the U.S. may not have been reliably tested for quality or authenticity due to a lack of affordable methods. Accordingly, a need exists for a cost-effective and scalable technique for ascertaining attributes of certain materials and without trained experts.

SUMMARY

The disclosed embodiments include at least one system, method, and apparatus for ascertaining attributes of sample material. A method includes mounting a handheld mobile device (e.g., smartphone) onto an external surface of a scanning device to capture images of samples placed on an internal surface of the scanning device. The captured images are communicated over a communications network to a service (e.g., cloud-based service) that can detect features in the captured images in accordance with artificial intelligence techniques to determine the attributes of the sample material (e.g., including impurities). The attributes of the sample material can be certified and communicated for display on the smartphone and/or shared with interested third-parties.

A portable scanning device includes an external mounting structure for holding a handheld mobile device that includes a camera such that the camera is positioned to capture multiple images of multiple samples that are each placed on an internal surface of the portable scanning device to determine an attribute of each of the samples. The portable scanning device further includes an internal chamber including the internal surface on which a particular sample is placed for capturing a particular image of the particular sample with the camera such that an optical distance from the camera to the internal surface and light radiated by a light source within the internal chamber enable capturing of the images of the samples to determine the attribute of each of the samples.

In some embodiments, the light source is a first light source of the handheld mobile device and/or a second light source integrated in the portable scanning device.

In some embodiments, the internal surface is adjustable to change a focal distance between the camera and the internal surface.

In some embodiments, the attribute is at least one of authenticity, purity, or quality of each of the samples.

This Summary is provided to introduce a selection of concepts in a simplified form that are further explained in the Detailed Description. This Summary is not intended to identify key features or essential features of the claimed subject matter, nor is it intended to be used to limit the scope of the claimed subject matter.

DETAILED DESCRIPTION

Figure 1A:
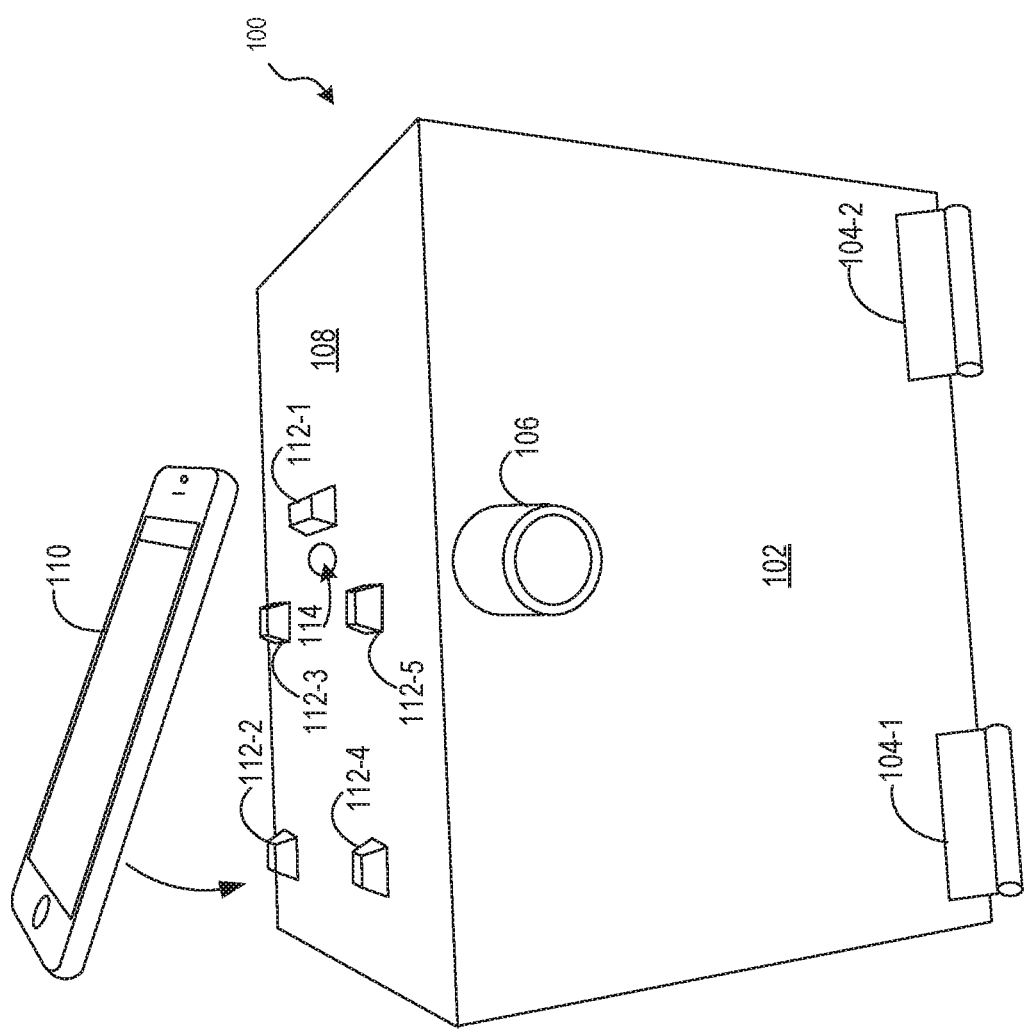
FIG. 1A illustrates a scanning device in a closed-door configuration that can capture images of sample material contained therein.

The embodiments set forth below represent the necessary information to enable those skilled in the art to practice the embodiments, and illustrate the best mode of practicing the embodiments. Upon reading the following description in light of the accompanying figures, those skilled in the art will understand the concepts of the disclosure and will recognize applications of these concepts that are not particularly addressed here. It should be understood that these concepts and applications fall within the scope of the disclosure and the accompanying claims.

The purpose of terminology used herein is only for describing embodiments and is not intended to limit the scope of the disclosure. Where context permits, words using the singular or plural form may also include the plural or singular form, respectively.

As used herein, unless specifically stated otherwise, terms such as "processing," "computing," "calculating," "determining," "displaying," "generating," or the like, refer to actions and processes of a computer or similar electronic computing device that manipulates and transforms data represented as physical (electronic) quantities within the computer's memory or registers into other data similarly represented as physical quantities within the computer's memory, registers, or other such storage medium, transmission, or display devices.

As used herein, terms such as "connected," "coupled," or the like, refer to any connection or coupling, either direct or indirect, between two or more elements. The coupling or connection between the elements can be physical, logical, or a combination thereof.

The various materials (e.g., plant material) that are sourced and used throughout developed and developing countries are typically pre-processed (e.g., dried, chopped, ground) before being traded in commerce. A processed material is typically mixed with other materials or substances (e.g., contaminants). Given the variety of materials found throughout the world and complexity of supply chains, ascertaining attributes such as authenticity, purity, and quality of materials is exceedingly important.

A conventional technique for ascertaining attributes of materials includes manual assessments by a skilled technician. This results in unreliable and inconsistent outcomes because different people assess plant materials in different ways. Sophisticated techniques that involve advanced technologies such as chemical, genetic, and other forms of analytical analysis provide consistent outcomes but are cost-prohibitive and accessible to only a small fraction of the entire commercial market.

The disclosed embodiments overcome these drawbacks with a standalone or distributed system that can utilize relatively inexpensive scanning devices that are distributed across the entire commercial market to uniformly ascertain attributes of widely distributed materials. The scanning device has a minimum number of mechanical and/or electronic components to stage samples of plant materials for capturing consistent images. The scanning device is not limited to ascertaining attributes of plant materials. Instead, the scanning device can analyze anything that fits in its chamber and that has at least one visual characteristic (e.g., color, size, shape, or texture) that can be detected by the camera but may be undetectable by an unaided human eye. It can analyze biological and/or non-biological materials such as finished foods and supplements and their ingredients, meats, fish, seafood, oils, beverages, cosmetics, gems, soil, etc.

In some embodiments, a handheld mobile device (e.g., mobile phone) is mounted on the scanning device to capture images of a sample contained within the scanning device. The mobile phone can be communicatively coupled to a service over a cellular or computer network. The disclosed embodiments can take advantage of the ubiquity of mobile phones in developed and developing countries to enable a process for reliably ascertaining the quality and authenticity of plant materials in a cost-effective manner. The backend service can be centralized or distributed to collect images of various materials. The images can be processed with an artificial intelligence system of the service to determine the quality and authenticity of the materials.

In some embodiments, a mobile application of the service allows users to ascertain the attributes of materials in commerce by using smartphones. The images captured by a smartphone are uploaded into a network portal on either the smartphone or a personal computer. To ensure consistency in image quality, the scanning device is designed for using a variety of mobile phones to capture images of materials that can be compared for training and analysis. That is, a variety of mobile phones can be calibrated to use the scanning device.

In some embodiments, image data is transferred via an application programming interface (API) to a cloud-based image recognition software program (e.g. Google Cloud Vision), which uses computer vision/machine learning to detect and classify features in the image data. Images that are used to develop an authentication database for ascertaining the attributes of materials are obtained with smartphones mounted on scanning devices that capture images of samples of materials that have been independently verified via any number of known methods (e.g., morphology, chemistry, and/or DNA sequencing).

The results that are output by the service are returned through an API to a local user interface of the handheld mobile device or computer. In some embodiments, a user can view resulting statistics and trends, and generate and share certificates of analyses. In some embodiments the images, sample information, and results are returned through an API to external software (e.g. supply-chain management or blockchain) for persistent storage. The disclosed embodiments include applications for authenticating plant and animal species, detecting adulteration and filth, assessing quality and manufacturing specifications, and tracking specific lots or samples through a supply chain. Further, the disclosed embodiments can be validated so that product suppliers and manufacturers can use it to comply with internal quality control specifications or other governmental regulations, such as the US Food and Drug Administration's current Good Manufacturing Practices.

At least some of the disclosed embodiments are the first known application of its kind designed for authentication and quality control evaluation of plant materials (e.g., herbs, spices) in their commercially traded forms (e.g., processed) such as dried, chopped, and powdered. Examples of existing technologies for plant species identification include PLANTSNAP, LIKETHATGARDEN, LEAFSNAP, FLOWERCHECKER, PLANTIFIER, NATUREGATE, AND IPFLANZEN. These technologies are designed to identify species based on a whole living plant, leaves, or flowers, not the commercially traded forms of plant materials. Further, images used to generate the reference databases are usually not verified by independent experts, or they are extracted from GOOGLE IMAGE searches. In contrast, the disclosed embodiments can use verified samples for reference images contained in the database.

Moreover, the disclosed embodiments uniquely provide a scanning device to ensure that the reference and test images are uniform. This allows the disclosed technology to detect subtle differences between samples that are not possible without taking images in a controlled environment, including controlled lighting, background color, sample placement, and focal distances.

The scanning device is portable, inexpensive, and designed for ascertaining the attributes of different types of materials. To this end, embodiments include a small and lightweight box composed of durable white, opaque, PVC, or other similar materials. The scanning device and associated trays have several advantageous features. For example, the scanning device eliminates external light, provide consistent internal lighting, consistent focal distance and background color, provides for consistent amounts of material, and ensures that sample materials are in the same position in a captured image so that software can consistently crop the captured images. The shelf distance to the handheld mobile device is adjustable to have the closest focal distance, to take clear high-quality images by using most smartphones. Moreover, a lower shelf allows for capturing images of larger-sized materials. In some instances, the shelf has a marker (e.g., a logo) printed on its surface to cause the camera to autofocus and for calibration. The marker can be essential for analyzing powdered, light-colored, or highly-processed materials because a camera cannot readily autofocus on these materials.

An embodiment includes a five-sided box with a hinged door on the bottom or side edge of the box. The box can have an approximate size of 200 mm (length)×150 (width)×125 (height). An internal chamber of the box can have removable lights (e.g., white, colored, incandescent, LED, ultraviolet (UV) or infrared (IR) light that are battery-powered and independently operable. A smartphone can be placed on the top of the box with its camera lens positioned over a one-inch hole into the chamber. The box has four legs, which are unnecessary if a knob or pull is not required to open the door. For example, the box can have a mechanism to press and release the door, or an indent, notch or handle on the side to open it. The chamber can hold shelf(s) for tray(s) that have compartments of different sizes and shapes for different materials. For example, whole objects or less-processed materials go on a larger compartment of a tray, small objects can sit on smaller compartments, and liquids or powders can be held in a small square compartment of a tray offset from the center. The camera lens can face directly inside the box to capture images by switching the smartphone to camera mode. The box does not require a special lens, interface, or optical device attached to the camera. Lastly, the image data can be uploaded to a cloud-based software through a web browser or native app on the smartphone for processing.

Figure 1B:
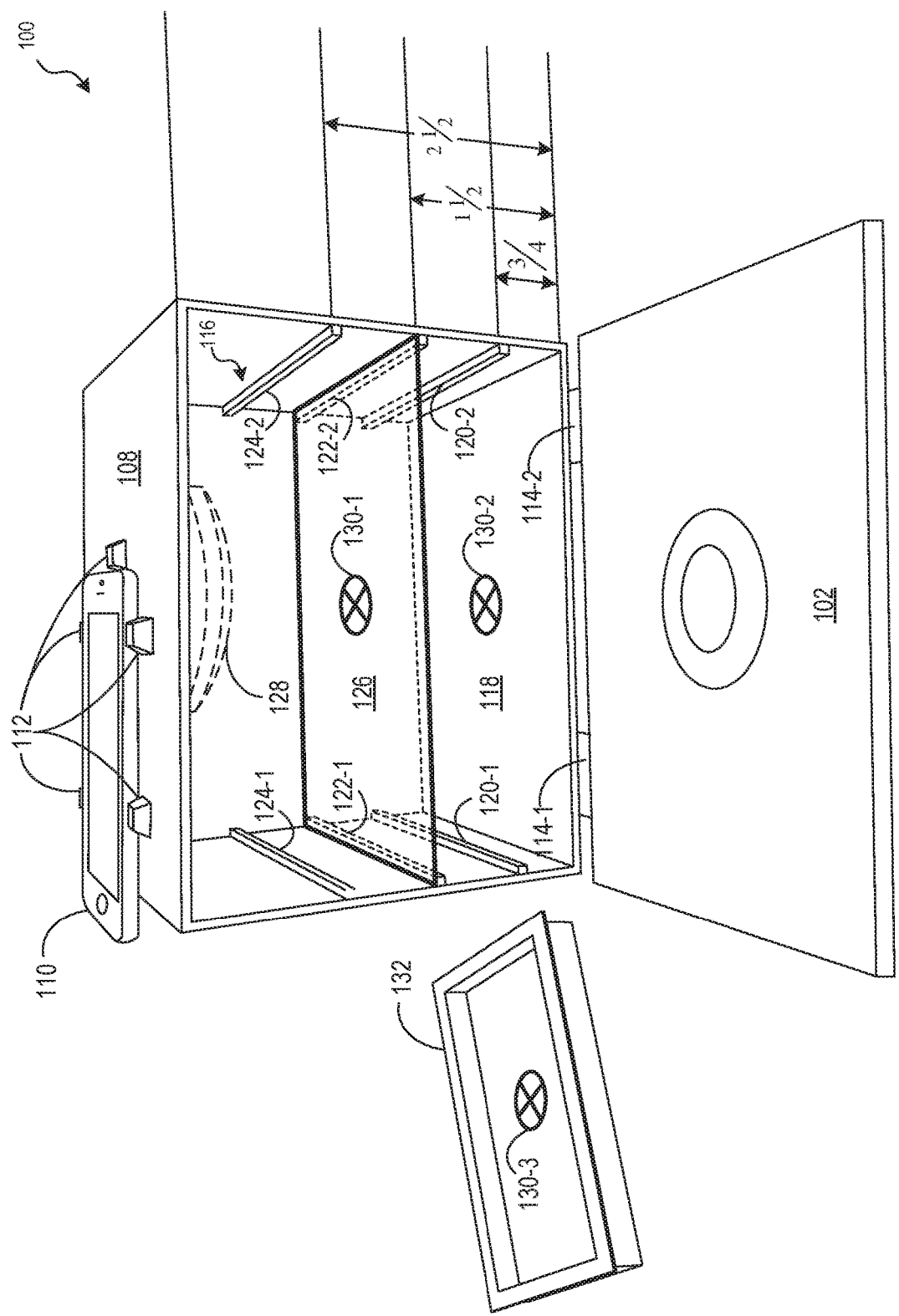
FIG. 1B illustrates the scanning device of FIG. 1A in an opened-door configuration.
Figure 1C:
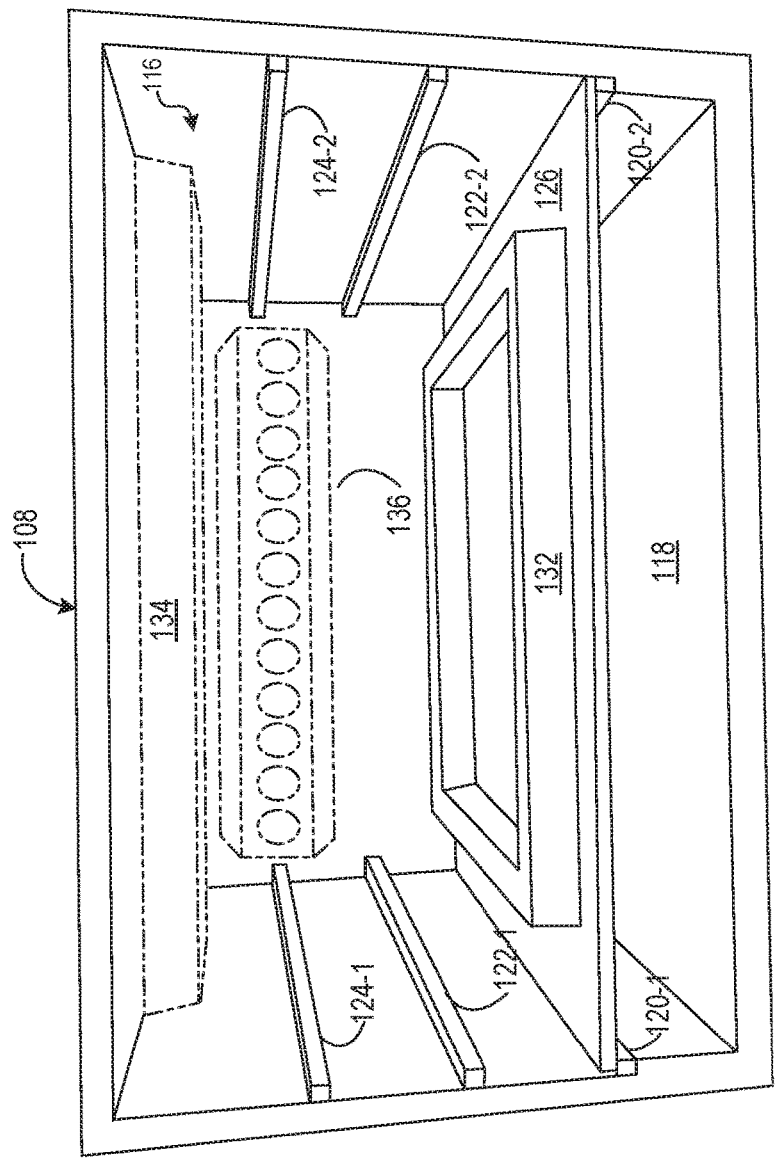
FIG. 1C illustrates a chamber of the scanning device of FIG. 1A.

For example, FIGS. 1A through 1C illustrate an embodiment of a scanning device 100. FIG. 1A illustrates the scanning device 100 in a closed-door configuration. As illustrated, the scanning device is a small, portable, and lightweight box that measures about 6"×6"×8". The scanning device 100 has a chamber (not shown) that functions as a controlled environment for capturing images of sample materials. The scanning device 100 includes an openable member 102 (e.g., a door) that enables access to the chamber. A shelf (not shown) inside the chamber can receive a tray with sample material. As illustrated, the openable member 102 is attached to scanning device 100 with hinges 104-1 and 104-2, and a handle 106 is used to open the openable member 102. The ambient light of an external environment is blocked from the chamber when the openable member is sealed closed. An exterior surface 108 of the scanning device 100 receives a handheld mobile device 110, which includes a camera device. The handheld mobile device 110 is secured to the exterior surface 108 with one or more positioners 112-1 through 112-5 that are shaped like bumps. An opening 114 through the exterior surface 108 to the chamber enables the handheld mobile device 110 to capture images of sample material when its camera lens is positioned over the opening 114.

FIG. 1B illustrates the scanning device 100 in an opened-door configuration. The chamber 116 can define level(s) for shelf(s) at predefined distances from the opening 114 (not shown) through the exterior surface 108. The shelf(s) are adjustable to change a focal distance to the camera. The floor 118 of the chamber 116 is furthest from the opening 114. The chamber 116 has support structures 120-1, 120-2, 122-1, 122-2, 124-1, and 124-2 that can support a removable shelf 126. For example, the level formed by the support structures 120-1 and 120-2 can support the shelf 126 at a predefined distance to the opening 114. Another level formed by the support structures 122-1 and 122-2 support the shelf 126 at another predefined distance, closer to the opening 114 compared to the level formed by the support structures 120-1 and 120-2. The support structures 124-1 and 124-2 can support the shelf 126 at a closest predefined distance to the opening 114 compared to the other predefined distances.

The scanning device 100 can use a light source of the handheld mobile device 110 to illuminate the sample material in the chamber 116. For example, the opening may be sufficiently large to allow light from a source of the handheld mobile device 110 to illuminate the sample material in the chamber 116. In some embodiments, the scanning device 100 includes a light source 128 that can radiate light on the sample material when disposed on the shelf 126. Examples of the light includes incandescent, LED, white, colored, ultraviolet (UV), or infrared (IR) light. As shown, the light source 128 is positioned on the ceiling of the chamber 116, has a circular shape, is removable, and faces the floor 118 of the chamber 116. The camera device of the handheld mobile device 110 faces the shelf 126 such that the light source 128 illuminates an area including the field-of-view of the camera.

FIG. 1C illustrates the chamber 116 with a combination of two or more removable light sources. For example, the light sources can be attached to the surfaces of the chamber 116 or inside surface of the door (not shown) by magnets. As shown, the down-facing light source 134 is positioned on the ceiling of the chamber 116, has an elongated shape, is removable, and faces the floor 118 of the chamber 116. The forward-facing light source 136 is positioned on the rear wall of the chamber 116, has a rectangular shape, is removable and faces the door (not shown) of the scanning device 100. Further, the forward-facing light source 136 is positioned to provide different amounts of light depending on the level at which the sample material is located. For example, the forward-facing light source 136 radiates more light at the level furthest from the floor 118 (closest to the opening 114 (not shown). The shelf 126 includes a marker 130 that enables the camera of the handheld mobile device 110 to autofocus on the shelf 126. The floor 118 also includes a marker 130-2 that enables the camera of the handheld mobile device 110 to autofocus on the floor 118.

The removable trays of the scanning device 100 can hold sample material, and the tray is placed on the shelf 126. For example, the main tray 132 can include a marker 130-3 that enables the camera of the handheld mobile device 110 to autofocus on the surface of the main tray 132. The scanning device 100 can utilize trays of different shapes and sizes that facilitate ascertaining attributes of different sample materials. The trays are washable, reusable, and can have a matte surface to reduce reflection. In most cases, the trays are white but could be black or other colors.

In one example, the main tray 132 can hold about 60 ml (¼ cup) of processed material across about a 4" by 5" area, hold a single object, or hold multiple small objects. The removable trays may be bigger/smaller trays depending on the shape and design of a chamber. As shown, the main tray has a raised lip around a rectangle in the center that holds the sample material. The area is optimized so that the camera of the handheld mobile device 110 takes a picture of the entire area without having to crop the edges of the captured image. Hence, the entire image can be analyzed to ascertain an attribute of the sample material.

Figure 4:
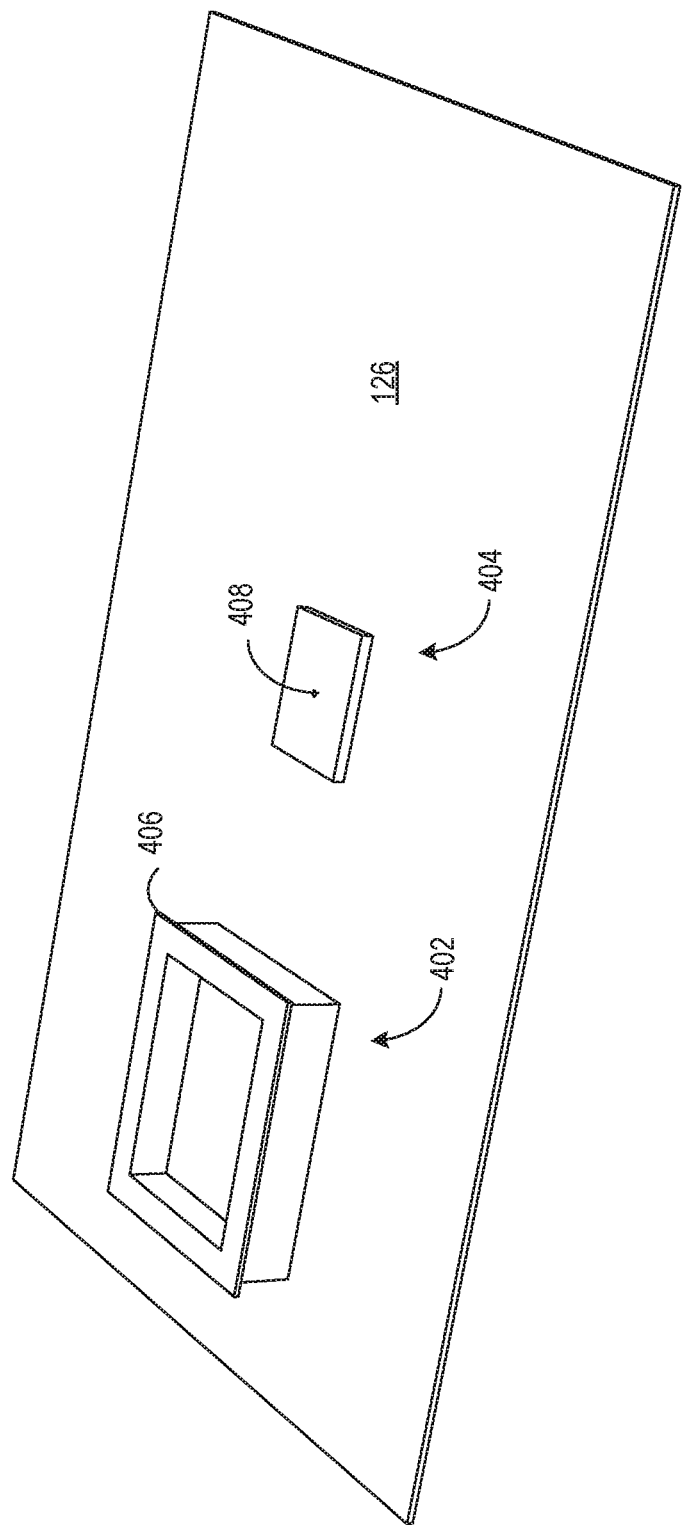
FIG. 4 illustrates a shelf with different trays thereon for sample materials.

FIG. 4 illustrates specialty trays that can hold different forms or amounts of sample materials. The specialty tray 402 is a small rectangle in the center or offset to hold smaller amounts of materials. This design can be optimized for 10 ml (2 teaspoons) of powder material or liquid and fit standard disposable weigh boats. The specialty tray 402 has a raised lip around the edges to put material on the tray. The specialty tray 404 is a flat square and/or has small dot on the center to place a relatively small object. The square for liquids is placed in an area on the tray to avoid light reflection or shadows from the hole on top. The image processing software can crop out areas of the tray that were captured in an image of the sample material.

Therefore, the four different level positions of the chamber 116 can hold the tray, depending on the size of the sample material and desired focal length from the camera. Once the sample material is placed at a level and the light source 128 is switched on, the openable member 102 is closed to seal the chamber from external light. The opening 114 on the top of the scanning device 100 then allows the camera to capture an image of the inside of the chamber 116 that contains the sample material. In some embodiments, another lens, such as a magnifying or microscopic lens is attached to the camera lens of the camera to augment the function of the camera.

The scanning device is not limited to the embodiments illustrated in FIGS. 1A through 1C. For example, a scanning device can have a carrying handle that folds in/out. The positioners 112 on the top of the scanning device can be adjustable to position different types of handheld mobile devices (e.g., smartphones, tablet computers). In some embodiments, one or more of the positioners 112 can be eliminated or removed. The scanner device can have integrated lights that run off a removable battery pack or plug into a wall outlet. In some embodiments, the scanning device has an integrated, rechargeable battery pack, an on/off switch/button, a hinged door or pull-out compartment, etc. The light sources can include white or colored LED or incandescent lights, ultraviolet (UV) or infrared (IR) lights. Moreover, an internal light source may be triggered to illuminate only when the door is closed, and/or the tray is inserted. In some embodiments, rather than having small legs, the scanning device has a larger base with a pull mechanism for an openable member.

Figure 2A:
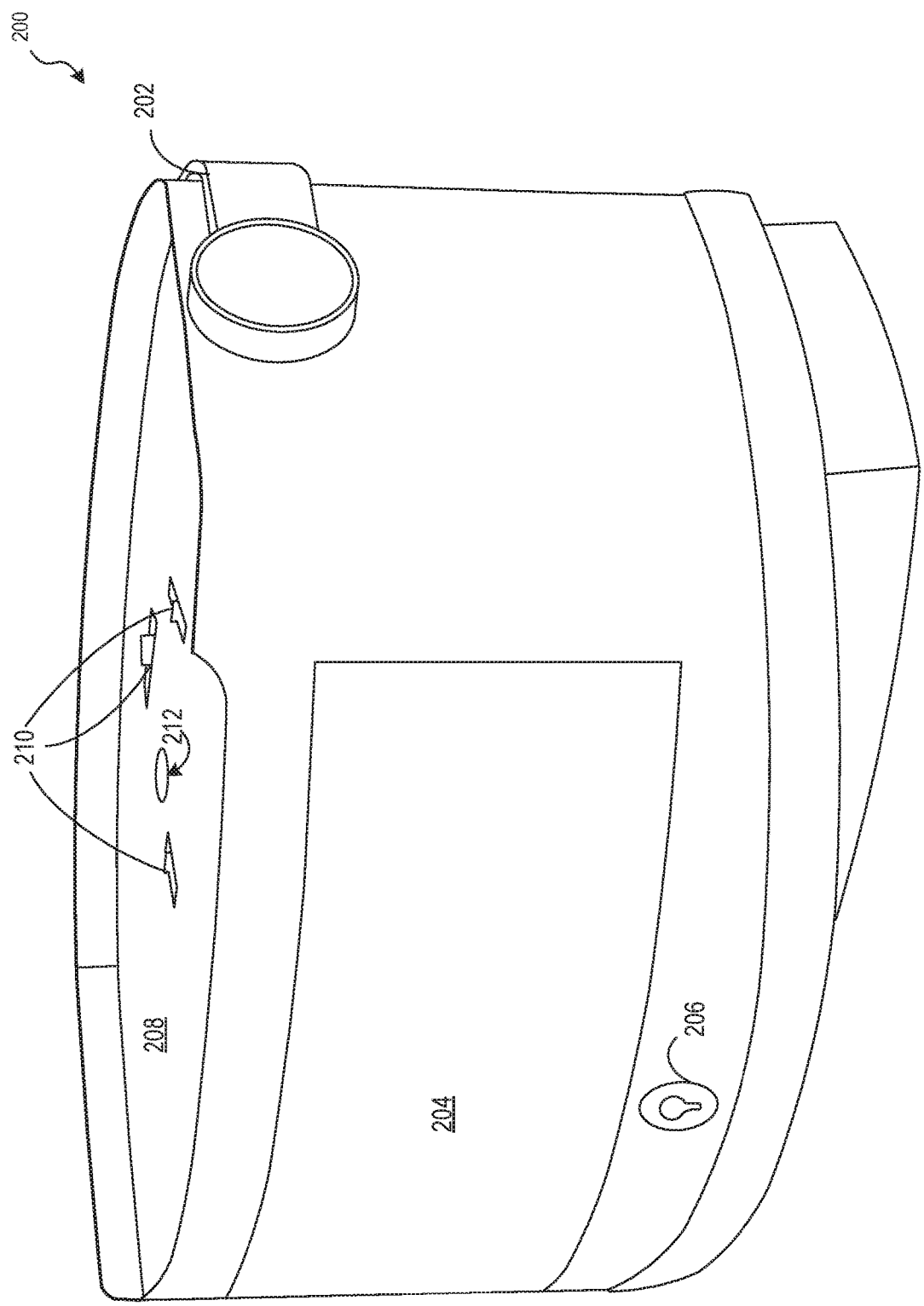
FIG. 2A illustrates a perspective view of another embodiment of a scanning device in a closed-door configuration.
Figure 2B:
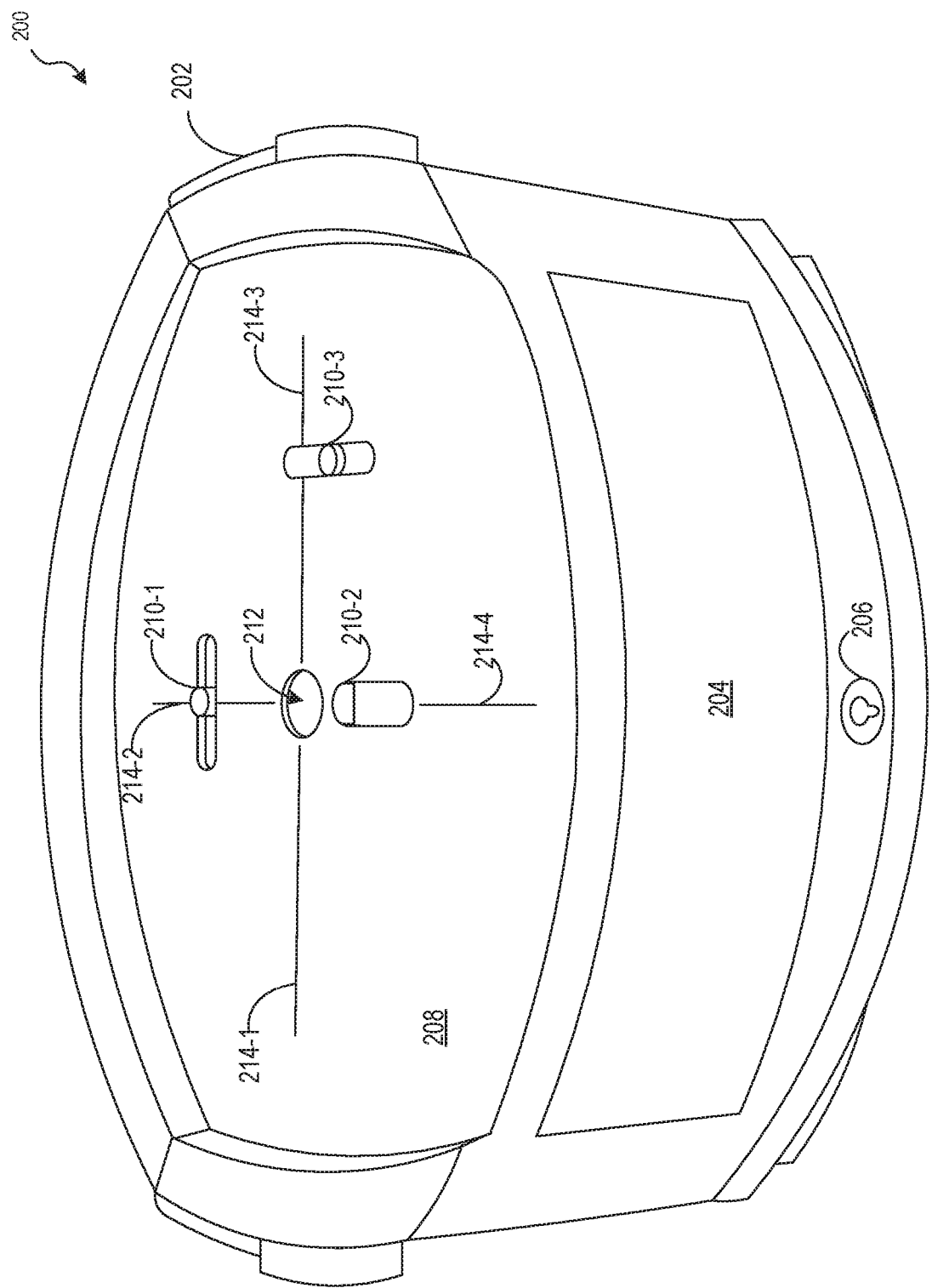
FIG. 2B illustrates a top-down view of the scanning device of FIG. 2A.
Figure 2C:
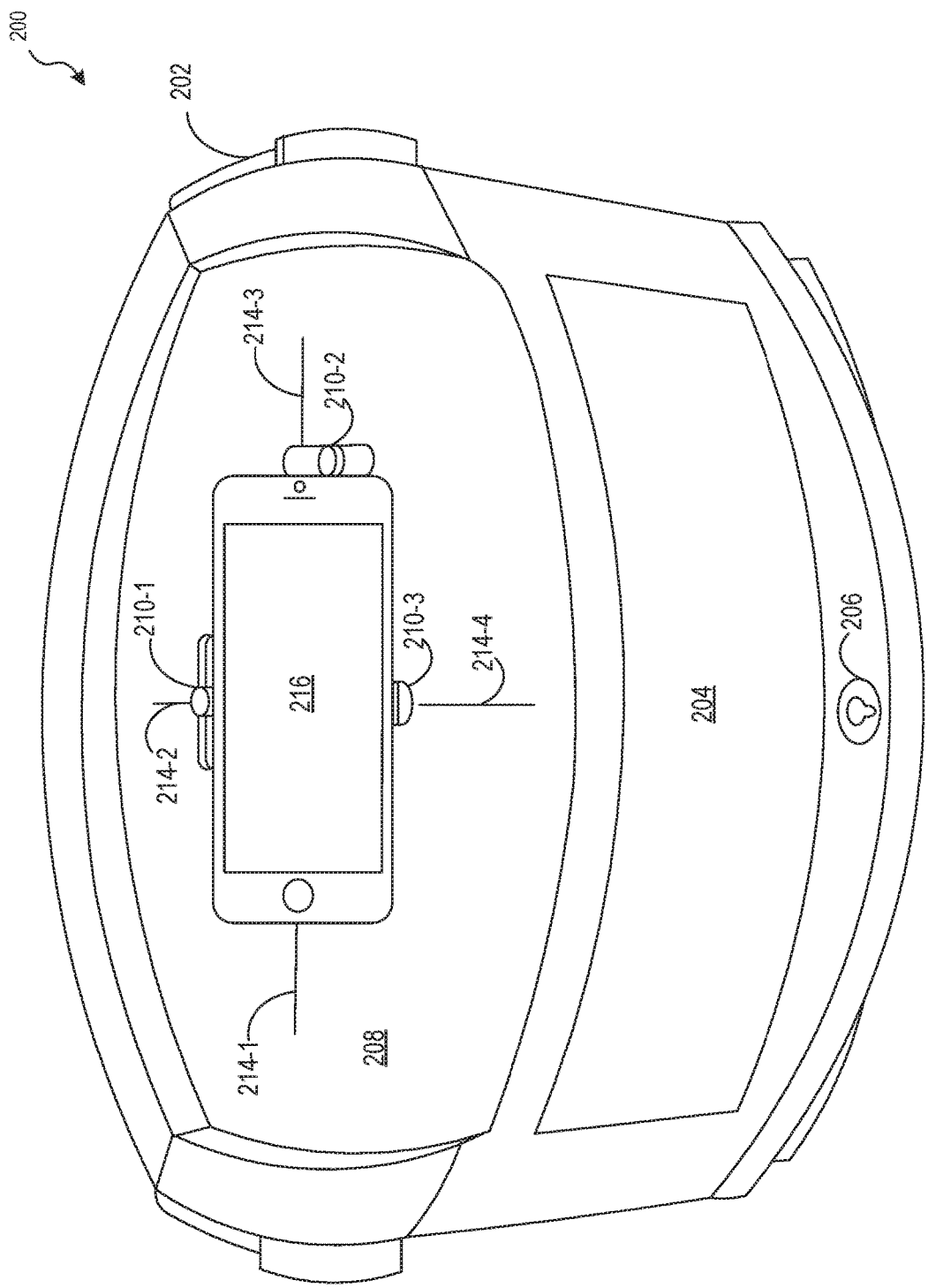
FIG. 2C illustrates the scanning device of FIG. 2A in a closed-door configuration with a handheld mobile device mounted thereon to capture images of sample material contained in a chamber of the scanning device.

FIGS. 2A through 2C illustrate another embodiment of a scanning device 200. Specifically, FIG. 2A illustrates a perspective view of the scanning device 200 with rounded edges in a closed-door configuration and FIG. 2B illustrates a top-down view of the scanning device 200. The scanning device 200 is portable and has a handle 202 for a user to carry the scanning device 200. The scanning device 200 has a chamber (not shown) that provides a controlled environment for capturing images of sample materials contained in the chamber. A push/pull openable member 204 allows a user to access the chamber. Similar to the previously described embodiments, sample material is placed on a tray that is placed on a removable shelf inside the chamber. As illustrated, a user can push a button 206 to open/close the openable member 204 to place/remove sample material. The light of an external environment is blocked from the chamber when the openable member 204 is closed.

An exterior surface 208 of the scanning device 200 can receive a handheld mobile device that includes a camera. The handheld mobile device is secured to the exterior surface 208 with one or more adjustable positioners 210-1 through 210-3. The positioners 210 are optional features that, in some embodiments, are unnecessary. For example, surface 218 can include markers to guide the user for positioning the handheld mobile device. An opening 212 through the exterior surface 208 to the chamber enables the camera of the handheld mobile device to capture the image of the sample material in the chamber. FIG. 2B also shows markers 214-1 through 214-4 that aid the user in positioning a handheld mobile device so that its camera is over the opening 212. FIG. 2C illustrates the scanning device 200 in a closed-door configuration with the handheld mobile device 216 mounted on the exterior surface 208 to capture an image of sample material contained in the chamber. As shown, the handheld mobile device 216 is positioned on the exterior surface 208 such that the camera of the handheld mobile device 216 is positioned over the opening and faces the shelf in the chamber.

In another embodiment, a camera is built-in a scanning device to capture images of samples without needing a separate handheld mobile device. The scanning device can also have a built-in interface such as a touchscreen on a top surface where the handheld mobile device normally sits. The scanning device itself may have a wireless interface to connect to Wi-Fi, cell service, and/or can connect to a handheld mobile device via, for example, BLUETOOTH. The scanning device can have a screen that allows one to see sample material inside the chamber and allow a user to control when to capture images and send image data to a handheld mobile device or upload to a remote computer system. In another embodiment, the built-in camera can be controlled by the handheld mobile device. The scanning device can identify a tray and/or type of material in the chamber to automatically select a correct cropping function.

Figure 3:
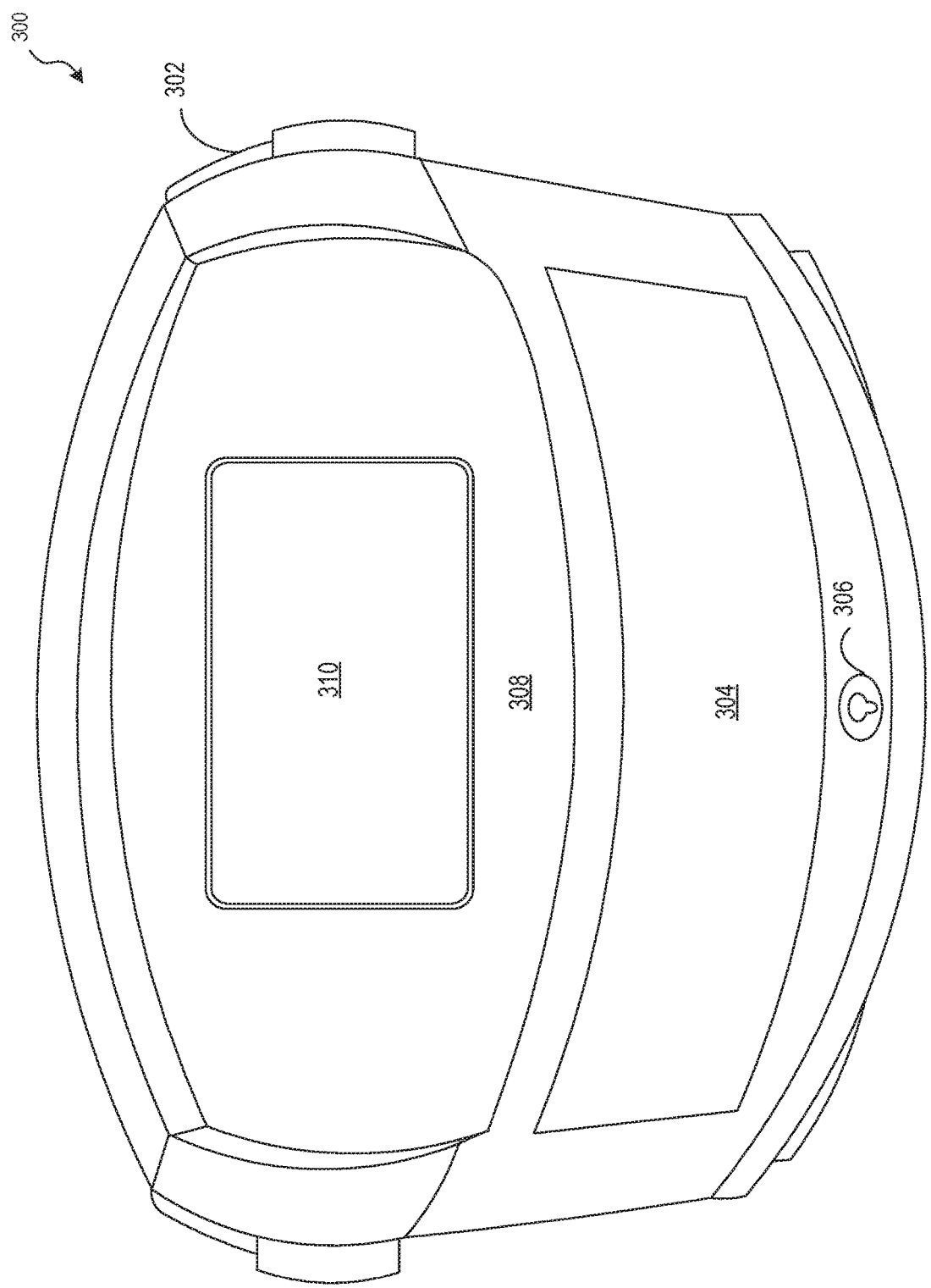
FIG. 3 illustrates another embodiment of a scanning device in a closed-door configuration with a built-in touchscreen to control a built-in camera to capture images of sample material contained in a chamber of the scanning device.

FIG. 3 illustrates an embodiment of a scanning device 300 in a closed-door configuration that includes a built-in touchscreen 310 and a built-in camera device (not shown) to capture images of sample material contained within a chamber (not shown). A user can control the built-in camera with the touchscreen 310. In some embodiments, the scanning device 300 is a standalone device that does not require a separate electronic device and/or network connectively to analyze sample material. The disclosed scanning devices can be part of a system that includes a server configured to process image data that is received over a network from a handheld mobile device or the scanner device. A remote server can determine an attribute of sample material based on the processed image data.

Figure 5:
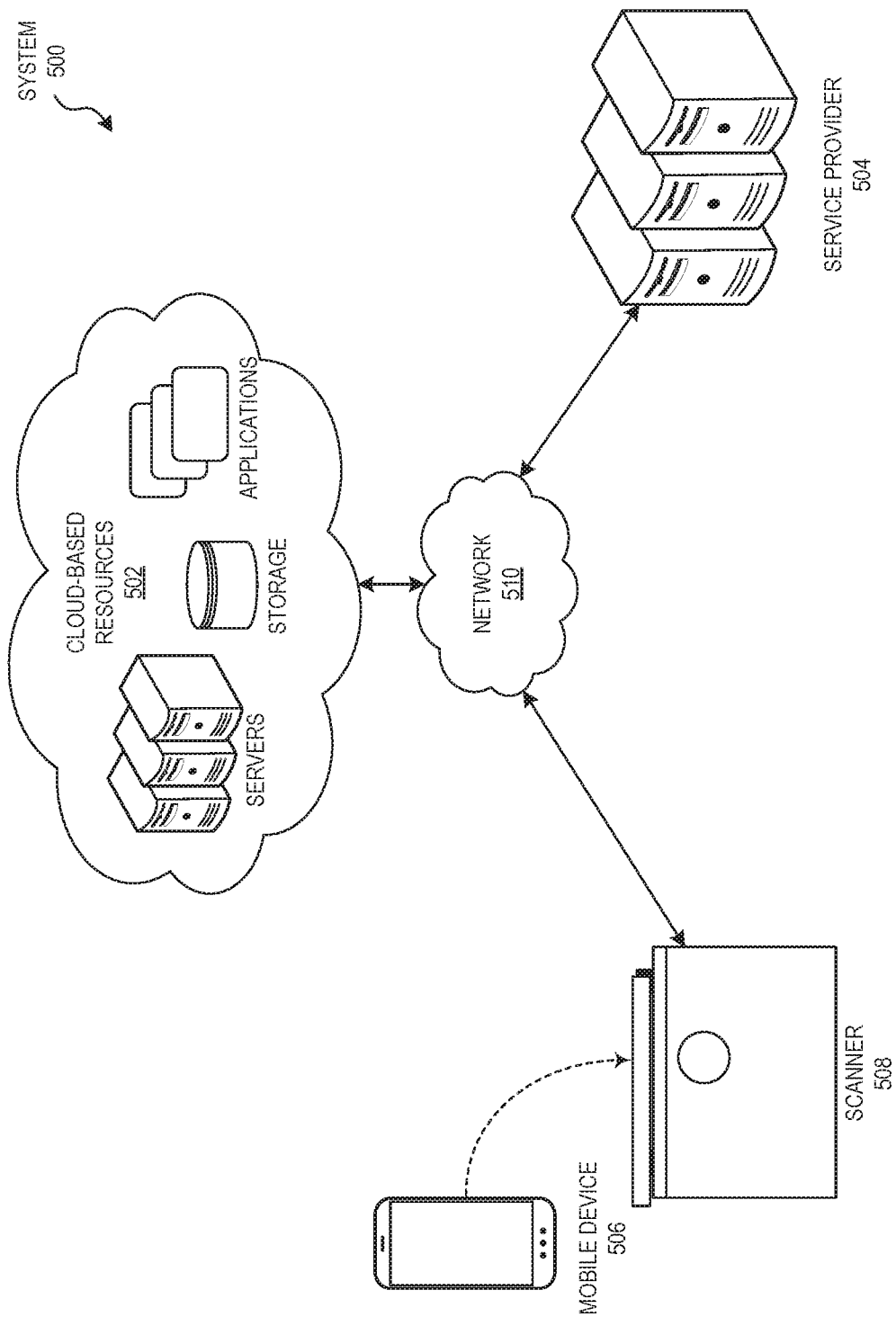
FIG. 5 is a block diagram that illustrates a system operable to ascertain attributes of sample material based on image data.

FIG. 5 is a block diagram of a system that can implement at least some aspects of the disclosed technology. The system 500 includes components such as cloud-based resources 502, one or more service provider servers 504 that use the cloud-based resources 502 to ascertain attributes of materials by the mobile phone 506 mounted on the scanning device 508, which are interconnected over a network 510, such as the Internet, to facilitate accurate testing of sample material.

The network 510 can include any combination of private, public, wired, or wireless portions. Data communicated over the network 510 may be encrypted or unencrypted at various locations or along different portions of the network 510. Each component of the system 500 may include combinations of hardware and/or software to process data, perform functions, communicate over the network 510, etc. For example, any component of the system 500 may include a processor, memory or storage, a network transceiver, a display, an operating system, and application software (e.g., for providing a user portal), etc. Other components, hardware, and/or software included in the system 500 are well known to persons skilled in the art and, as such, are not shown or discussed herein.

The cloud-based resources 502 can provide access to a shared pool of configurable computing resources including servers, storage, applications, software platforms, networks, services, etc. The cloud-based resources 502 are accessible by the service provider servers 504 to offer resources to the mobile phone 506, which is mountable on the scanning device 508. The service provider servers 504 may include any number of computing devices that provide applications for services that allow users to ascertain the quality and authenticity of plant material. Although shown separate from the cloud-based resources 502, the service provider servers 504 may be part of the cloud-based resources 502.

The cloud-based resources 502 can facilitate processing image data of samples captured by the mobile phone 506 mounted on the scanning device 508. For example, the service provider servers 504 can train a machine learning model and implement that machine learning model to ascertain the quality and authenticity of plant material. The analysis may involve analyzing the physical attributes of plant material captured in an image.

The mobile phone 506 is operated by a user that interacts with the system 500. An example of the mobile phone 506 is a smartphone (e.g., APPLE (PHONE, SAMSUNG GALAXY), or any other handheld mobile device with a camera that is capable of being calibrated for capturing reliable images of samples to enable ascertaining attributes of a captured image of a sample material. The mobile phone 506 is also capable of communicatively coupling with the service provider servers 504 over the network 510. In some embodiments, any images of sample material captured at the scanning device can be processed locally at the scanning device with local hardware and software that is loaded at the handheld mobile device 506 or some other local computing device. In other words, at least some of the functions performed by the cloud-based resources 502 and/or the service provider 504 can be performed locally at the scanning device 508.

The disclosure is not limited to a smartphone mounted on a separate scanning device. Examples of other suitable handheld mobile devices that can be mounted on the scanning device 508 include laptop computers (e.g., APPLE MACBOOK, LENOVO 440), tablet computers (e.g., APPLE IPAD, SAMSUNG NOTE, MICROSOFT SURFACE), or any other handheld mobile device that has an adequate camera and capabilities to communicate over the network 510. In some embodiments, the scanning device 508 is a specialized device that has the components of the mobile phone 506 necessary to practice the disclosed embodiments.

In some embodiments, the service provider servers 504 provide or administer a user interface (e.g., website, app) accessible from the mobile phone 506. The user interface may include menu items for selecting image capture and/or processing operations and to present analytics about the quality and authenticity of plant material. The user interface may also provide certificates of authenticity that can be shared with interested third-parties.

To provide reliable results regarding the quality, purity, or authenticity of sample material, the disclosed embodiments can implement artificial intelligence techniques based on a broad range of images collected from diverse sources, and images of materials that have been authenticated by other generally accepted techniques such as morphological, chemical, and/or genetic analysis. In one example, the disclosed embodiments implement computer vision/machine learning (CV/ML) technology to ascertain the attributes of sample material. Specifically, users can upload images of sample material with their mobile phones to a service that is remotely located from the locations where images were captured. The users can receive results from the service on their same mobile phones, a tablet computer or on any other computing device.

The service can be built on top of a unified platform. Hence, the disclosed architecture gives a broad range of customers access to a service by using mobile phones or other devices (e.g., tablet computer, personal computer) and networks that are ubiquitous in even remote parts of the world and may only require access to a relatively inexpensive scanning device to normalize the images of the sample materials for reliable, consistent, and trusted results. For example, the disclosed solution can be deployed with cloud resources to take full advantage of the cloud's flexibility and scalability. The solutions and cloud resource management are both provided via a simple user interface. This allows administrators to allocate resources as needed, and to start/stop servers at a chosen schedule. The combination of unique computer vision technology and scalable platform on the cloud allows for the rapid development of accurate and robust solutions to enhance an authentication process.

The disclosed CV/ML technology is trained with authenticated images of diverse materials that have been preprocessed according to acceptable commercial practices. The training images can include combinations of materials, impurities, and contaminants for detection in subsequent samples. Hence, the service combines computer vision and deep learning technology on a scalable platform to bring affordable and unique capabilities to users throughout the world. In some embodiments, the disclosed technology implements a variety of image recognition algorithms that combine both image matching with deep learning. This combination allows the algorithms to complement each other in order to maximize performance and accuracy.

In some embodiment, the service defines metadata, which includes attributes used to detect and identify material and impurities. In some embodiments, the authentication service is continuously trained by capturing training images obtained from various sources and that include material that has been authenticated in accordance with traditional techniques. The training images can be uploaded by a variety of means to extract features that are labeled and stored as labeled features in a database. Examples of labeled features include species, plant or animal part, or a variety of physical properties such as colors, dimensions, densities, etc. In some examples, objects such as rocks, sticks, and rodent excreta are labeled. In some embodiments, the labeling of images and features in a training set is done automatically with detection methods and/or manually with skilled workers to provide a uniform and consistent assessment of tested material.

In some embodiments, the training of the authentication service involves setting-up training parameters that are continuously adjusted to control the efficiency and accuracy of processing. For example, a training job can be launched periodically based on images of authenticated plant materials to routinely update and adjust an authentication database. The database could be tested and/or recalibrated for accuracy by periodically submitting images of authenticated plant materials of known quality and impurities.

As such, the service can detect a range of materials and impurities to suggest relevant labels for recognizable features. A combination of recognizable features detected in an image can be used to identify the attributes of sample materials. The service can be deployed on a variety of networks including servers that are located in a centralized location or in a decentralized architecture such as a blockchain network that ensures the reliability of results with sophisticated fault tolerance. In some embodiments, a cluster of servers is configured to run and scale the service as needed. The service could also include an API integration for a variety of applications to further increase the usability of the service.

In some embodiments, the service can implement an artificial intelligence technique that follows vision processing of conventional skilled workers but in a way that ensures uniformity for reliably accurate results. For example, a convolutional neural network (CNN) could emulate the response of an individual neuron to visual stimuli, where each convolutional neuron processes data for its receptive field. Although fully connected feedforward neural networks can learn features as well as classify data, it is not necessarily practical to apply this architecture to images because a very large number of neurons would be necessary due to the very large input sizes associated with images, where each pixel is a relevant variable. The convolution operation of a CNN solves this problem because it reduces the number of free parameters. For example, regardless of image size, tiling regions of size 5×5, each with the same shared weights, requires only 25 learnable parameters. In this way, a CNN can resolve the problems that occur when training traditional neural networks with many layers by using backpropagation. As such, a CNN can reliably find patterns in images to ascertain the attributes of sample materials.

Figure 6:
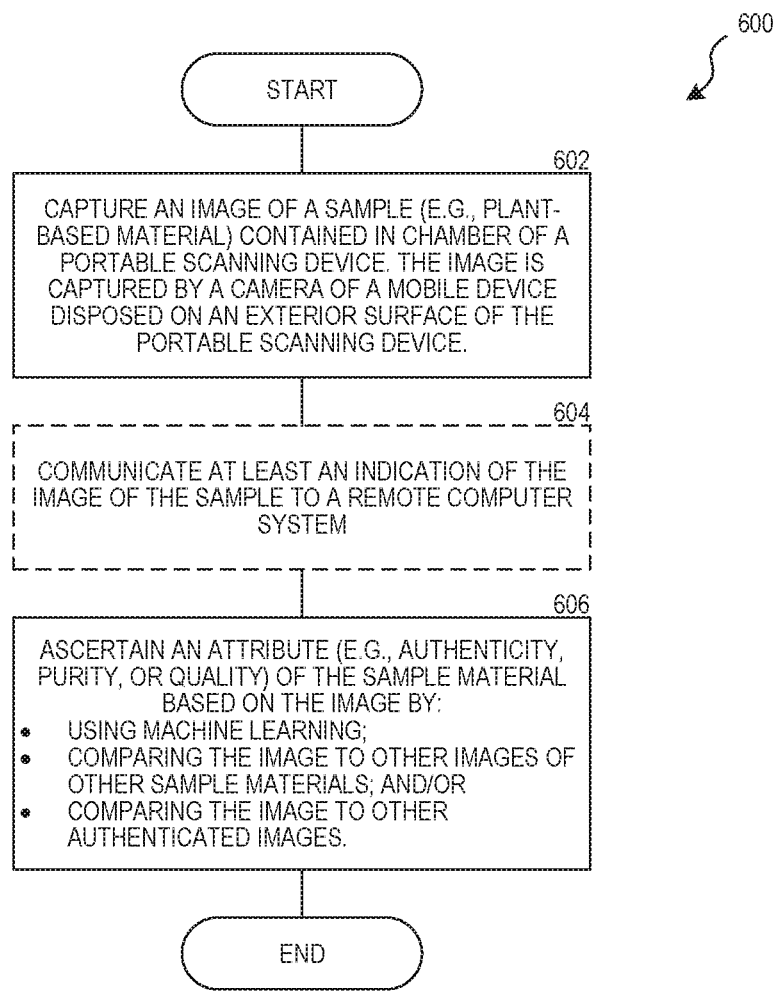
FIG. 6 is a flowchart that illustrates a method performed by a scanning device to ascertain an attribute of sample material.

FIG. 6 is a flowchart that illustrates a method performed by a scanning device to ascertain an attribute of sample material. In step 602, the handheld mobile device captures an image of a sample material contained in an enclosed chamber of a portable scanning device. The image is captured by a camera of a mobile device when disposed on an exterior surface of the portable scanning device.

In step 604, the handheld mobile device can communicate image data indicative to a remote computer system. The remote computer system analyzes the image data to ascertain one or more attributes of the sample material. The remote computer system then returns results over the network to the handheld mobile device.

In step 606, the handheld mobile device itself can ascertain an attribute of sample material based on image data. In some embodiments, the sample material is a plant-based material. The attribute of the plant-based material is ascertained in accordance with machine learning techniques as described elsewhere in this description. In some embodiments, the attribute of the sample material is ascertained by comparing the captured image to image data of multiple sample materials. In some embodiments, the attribute is ascertained by comparing the image data to images of authenticated images including other images of the same sample.

Figure 7:
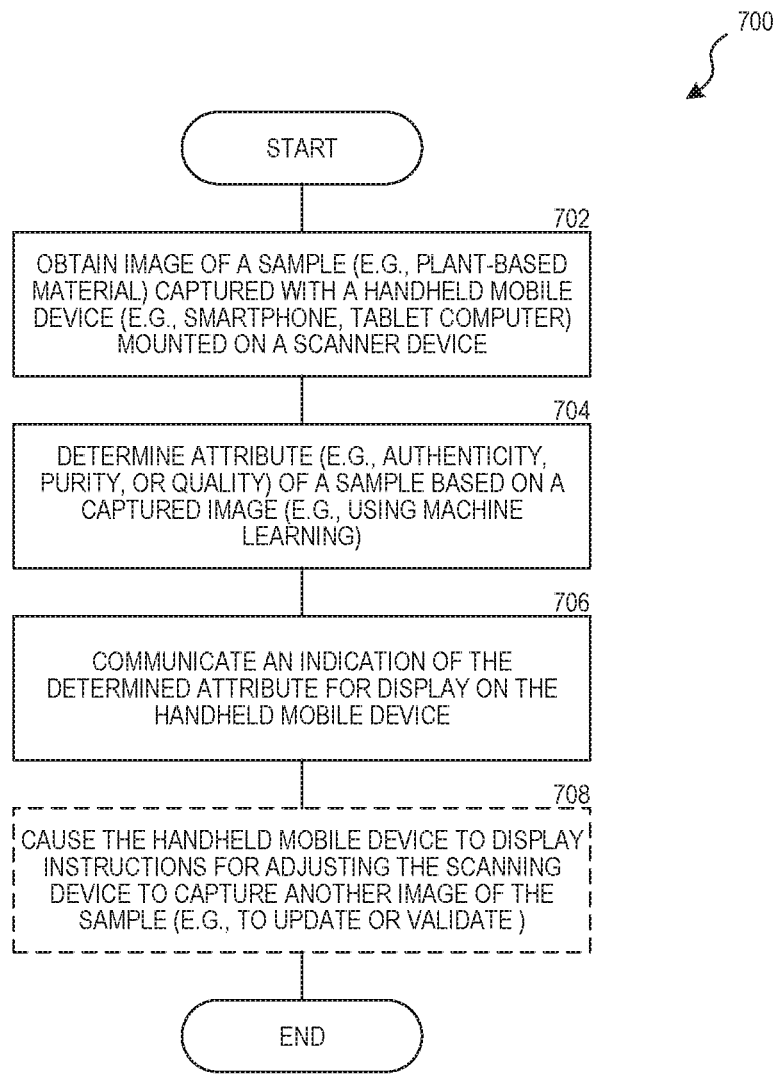
FIG. 7 is a flowchart that illustrates a method performed by a system including a scanning device to ascertain an attribute of sample material.

FIG. 7 is a flowchart that illustrates a method performed by a system including a scanning device to ascertain an attribute of sample material. In step 702, a service obtains, over a communications network, image data obtained with a camera of a handheld mobile device mounted on a scanning device. In some embodiments, the method is performed at least in part by a cloud-based service that is communicatively coupled to the handheld mobile device over the communications network.

In step 704, the service determines one or more attributes of the sample based on a combination of visual features detected in the captured image of the sample. In some embodiments, the sample includes at least one plant material and a non-plant contaminant. In some embodiments, the quality, purity, or authenticity of the plant material is determined in accordance with machine learning techniques. In some embodiments, determining the quality, purity, or authenticity of the sample includes detecting the visual features in the captured image of the sample, and identifying contents of the sample based on the combination of detected visual features. In some embodiments, the entire image is classified, or some, part, or a portion of the image is classified (e.g., a cropped image). In some embodiments, the system can detect specified objects and can count a quantity of the specified object.

In step 706, the service communicates the ascertained attributes of the sample material over the communications network to the handheld mobile device. In optional step 708, the service can cause the handheld mobile device to display instructions and/or automatically adjust the camera to capture another image of the sample material or to adjust and/or validate an ascertained attribute.

Figure 8:
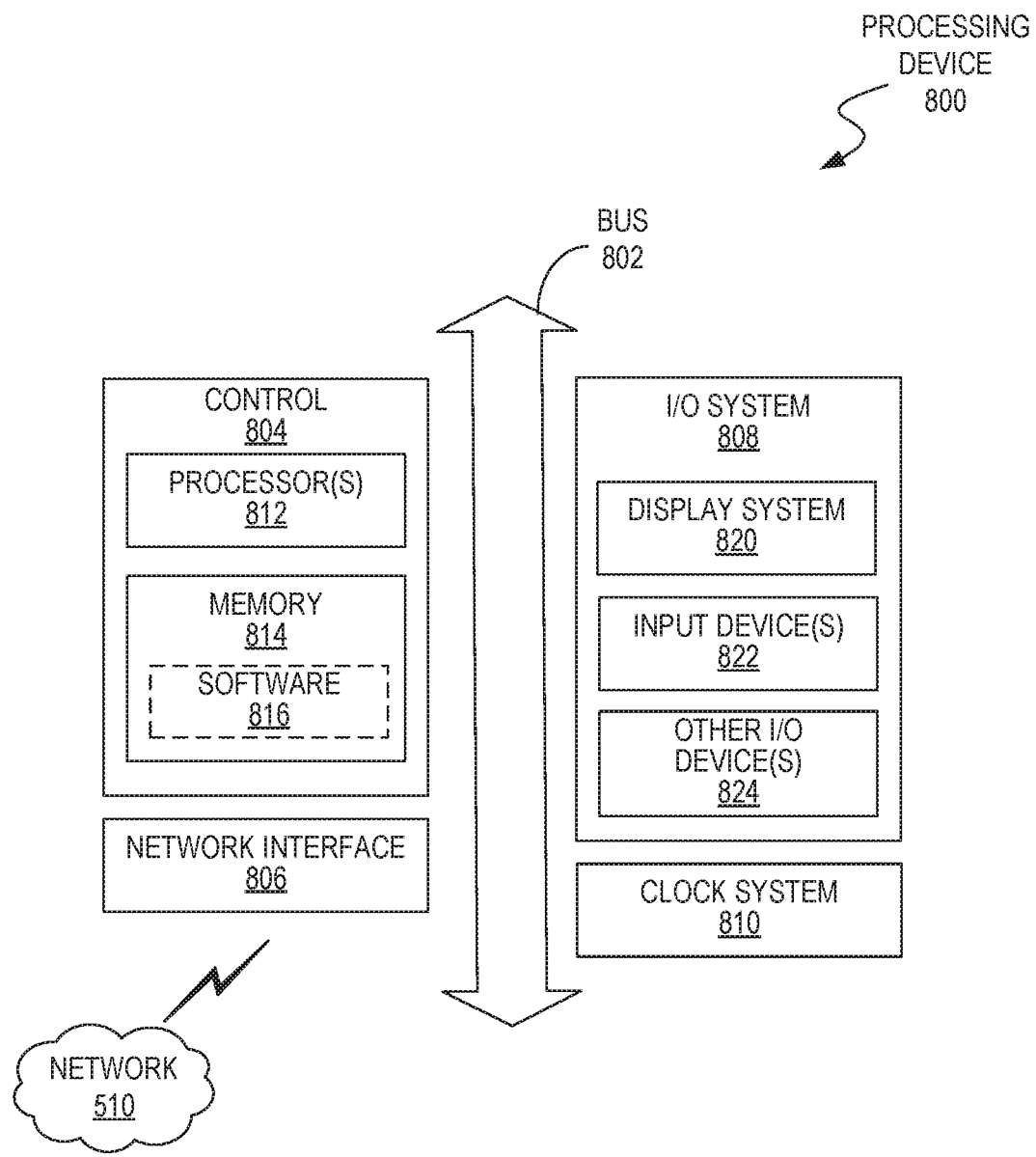
FIG. 8 is a block diagram that illustrates a processing device operable to implement at least some aspects of the disclosed technology.

FIG. 8 is a block diagram that illustrates a processing device 800 (e.g., scanning device or service server) operable to implement the disclosed technology. As shown, the processing device 800 includes a bus 802 that is operable to transfer data between hardware and/or software components. These components include a control 804 (e.g., processing system), a network interface 806, an input/output (I/O) system 808, and a clock system 810. The processing device 800 may include other components that are not shown nor further discussed for the sake of brevity. One of ordinary skill in the art will understand any hardware and software that is included but not shown in FIG. 8.

The control 804 includes one or more processors 812 (e.g., central processing units (CPUs)), application-specific integrated circuits (ASICs), and/or field-programmable gate arrays (FPGAs), and memory 814 (which may include software 816). For example, the memory 814 may include volatile memory, such as random-access memory (RAM) and/or non-volatile memory, such as read-only memory (ROM). The memory 814 can be local, remote, or distributed.

A software program (e.g., software 816), when referred to as "implemented in a computer-readable storage medium," includes computer-readable instructions stored in the memory (e.g., memory 814). A processor (e.g., processors 812) is "configured to execute a software program" when at least one value associated with the software program is stored in a register that is readable by the processor. In some embodiments, routines executed to implement the disclosed embodiments may be implemented as part of operating system (OS) software (e.g., MICROSOFT WINDOWS, LINUX) or a specific software application, component, program, object, module, or sequence of instructions referred to as "computer programs."

As such, computer programs typically comprise one or more instructions set at various times in various memory devices of a computer (e.g., processing device 800), which, when read and executed by at least one processor (e.g., processor 812), will cause the computer to perform operations to execute features involving the various aspects of the disclosed embodiments. In some embodiments, a carrier containing the aforementioned computer program product is provided. The carrier is one of an electronic signal, an optical signal, a radio signal, or a non-transitory computer-readable storage medium (e.g., memory 814).

The network interface 806 may include a modem or other interfaces (not shown) for coupling the processing device 800 to other computers over the network 510. The I/O system 808 may operate to control various I/O devices, including peripheral devices such as a display system 820 (e.g., a monitor or touch-sensitive display) and one or more input devices 822 (e.g., a keyboard and/or pointing device). Other I/O devices 824 may include, for example, a disk drive, printer, scanning device, or the like. Lastly, the clock system 810 controls a timer for use by the disclosed embodiments.

Operation of a memory device (e.g., memory 814), such as a change in state from a binary one (1) to a binary zero (0) (or vice versa) may comprise a visually perceptible physical change or transformation. The transformation may comprise a physical transformation of an article to a different state or thing. For example, a change in state may involve accumulation and storage of charge or a release of stored charge. Likewise, a change of state may comprise a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

While embodiments have been described in the context of fully functioning computers, those skilled in the art will appreciate that the various embodiments are capable of being distributed as a program product in a variety of forms and that the disclosure applies equally, regardless of the particular type of machine or computer-readable media used to actually effect the embodiments.

While the disclosure has been described in terms of several embodiments, those skilled in the art will recognize that the disclosure is not limited to the embodiments described herein and can be practiced with modifications and alterations within the spirit and scope of the invention. Those skilled in the art will also recognize improvements to the embodiments of the present disclosure. All such improvements are considered within the scope of the concepts disclosed herein. Thus, the description is to be regarded as illustrative instead of limiting.

We claim:
1. A system comprising:
a portable scanning device including:
  a chamber configured as a controlled environment for capturing an image of a sample material contained in the chamber;
  an openable member configured to enable access to the chamber, wherein ambient light of an external environment is blocked from the chamber when the openable member is closed;
  an exterior surface configured to receive a handheld mobile device that includes a camera device;
  an opening through the exterior surface into the chamber to enable the camera device of the handheld mobile device to capture the image of the sample material when the handheld mobile device is disposed on the exterior surface such that the camera device is to face into the chamber;
  a shelf configured to stage the sample material at a distance from the opening thereby enabling the camera device to capture the image of the sample material at a resolution to detect physical properties of the sample material including a plurality of colors, sizes, shapes, or textures;
  a removable tray configured to position on the shelf, the removable tray including a container with a staging surface defining an area configured to stage the sample material for the image, and the area having a size such that a field-of-view of the camera device disposed on the exterior surface includes the area; and
  a white light source configured to illuminate the sample material disposed on the area such that the image is of the sample material illuminated by the white light.
2. The system of claim 1 further comprising:
a server configured to:
  process data of the image, wherein the data of the image is received over a network from the handheld mobile device; and
  determine the physical properties of the sample material based on the processed data of the image.
3. The system of claim 1 further comprising:
a support structure that defines a first level of a plurality of levels for the shelf, wherein each level is at a predefined distance from the opening.

4. The system of claim 3, wherein a second level of the shelf is a surface of the chamber.

5. The system of claim 1, wherein the white light source is a removable device.

6. The system of claim 1, wherein the shelf comprises:
a marker that enables the mobile device to autofocus the camera device.

7. The system of claim 1, wherein the removable tray comprises:
a marker that enables the handheld mobile device to automatically focus the camera device.

8. The system of claim 1 further comprising:
a plurality of removable trays of different sizes, wherein each of the plurality of removable trays is configured to hold a different type of sample material.

9. The system of claim 1, wherein the exterior surface comprises:
a plurality of positioners configured to orient the handheld mobile device for capturing the image of the sample material with the camera device.

10. The system of claim 9, wherein a positioner is adjustable to fit a plurality of handheld mobile devices of different sizes.

11. A method comprising:
radiating light on a sample material disposed on a staging surface of a platform contained in an enclosed chamber of a portable scanning device,
capturing an image of the sample material disposed on the staging surface of the platform contained in the enclosed chamber of the portable scanning device,
wherein the image is captured by a camera device of a mobile device disposed on an exterior surface of the portable scanning device,
wherein the platform has an aspect-ratio such that a field-of-view of the camera device disposed on the exterior surface includes the staging surface, and
wherein the platform is at a distance from the camera device to provide a resolution of properties of the sample material; and
ascertaining an attribute of the sample material based on the image,
wherein the attribute includes authenticity, purity, or quality of the sample material.

12. The method of claim 11, wherein the sample material is a biological material.

13. The method of claim 11, wherein the sample material is a plant-based material, and the attribute of the plant-based material is determined in accordance with machine learning techniques.

14. The method of claim 11, wherein ascertaining the attribute of the sample material comprises:
comparing the image to data of another image of the sample material to verify the attribute.

15. The method of claim 11, wherein ascertaining the attribute of the sample material comprises:
comparing the image to data of a plurality of images of authenticated samples.

16. A portable scanning device comprising:
a chamber configured as a controlled environment for capturing an image of a sample material contained in the chamber;
an openable member configured to enable access to the chamber for receiving the sample material, wherein ambient light of an environment external to the chamber is blocked from the chamber when the openable member is closed; and
an imaging device configured to capture the image of the sample material when disposed on a shelf contained in the chamber, the shelf being configured to stage the sample material at a distance from the imaging device thereby enabling the imaging device to capture the image of the sample material at a resolution to detect physical properties of the sample material including a plurality of colors, sizes, shapes, or textures of the sample material; and
a light source configured to radiate light on the sample material disposed on the shelf such that the image is of the sample material exposed to the light.

17. The portable scanning device of claim 16 further comprising:
a touchscreen integrated in an exterior surface of the scanning device, wherein the touchscreen enables a user to control the imaging device.

18. The portable scanning device of claim 16, wherein the imaging device is a camera integrated in a surface of the chamber and facing the shelf.

19. A method comprising:
illuminating a sample on a tray disposed on a shelf of a scanning device, the tray including an area to stage the sample and having a size such that a field-of-view of a camera of a handheld device that is mounted on the scanning device includes the area;
obtaining, over a communications network, an image of the sample captured with the camera of the handheld mobile device that is mounted on the scanning device, the image providing a resolution of physical features of the sample, the physical features including a plurality of colors, sizes, shapes, or textures of the sample;
determining an attribute of the sample based on a combination of the physical features detected in the captured image of the sample; and
communicating, over the communications network, an indication of the determined attribute of the sample for display on the handheld mobile device.

20. The method of claim 19, wherein the sample includes at least one plant material and a non-plant contaminant.

21. The method of claim 20, wherein the attribute of the plant material is determined in accordance with machine learning techniques.

22. The method of claim 19, wherein the handheld mobile device is a smartphone or tablet computer.

23. The method of claim 19 further comprising:
causing the handheld mobile device to adjust the camera and capture another image of the sample to adjust or validate the determined attribute of the sample.

24. The method of claim 19 further comprising:
causing the handheld mobile device to display instructions for adjusting the scanning device and capture another image of the sample to update or validate the determined attribute of the sample.

25. The method of claim 19, wherein determining the attribute of the sample comprises:
detecting the physical features in the captured image of the sample; and
identifying contents of the sample based on the combination of detected physical features.

26. The method of claim 19, wherein the method is performed by a cloud-based service communicatively coupled to the handheld mobile device over the communications network.

27. The system of claim 1, wherein the removable tray includes a plurality of raised sides that define the container, the staging surface is flat and matte, and the area is a rectangular.

28. The system of claim 1, wherein the detected physical properties of the sample material are indicative of an attribute including authenticity, purity, or quality of the sample material.

29. The method of claim 11, wherein the radiated light includes at least one of white or colored LED or incandescent light, ultraviolet (UV) light, or infrared (IR) light.

* * * * *